(12) United States Patent
Sato

(10) Patent No.: US 9,867,545 B2
(45) Date of Patent: Jan. 16, 2018

(54) ACOUSTIC WAVE MEASURING APPARATUS AND CONTROL METHOD OF ACOUSTIC WAVE MEASURING APPARATUS

(71) Applicant: CANON KABUSHIKI KAISHA, Tokyo (JP)

(72) Inventor: Akira Sato, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 683 days.

(21) Appl. No.: 13/649,672

(22) Filed: Oct. 11, 2012

(65) Prior Publication Data

US 2013/0116537 A1 May 9, 2013

(30) Foreign Application Priority Data

Nov. 4, 2011 (JP) ................................. 2011-242271

(51) Int. Cl.
*A61B 8/00* (2006.01)
*A61B 5/00* (2006.01)
*A61B 8/08* (2006.01)

(52) U.S. Cl.
CPC ............ *A61B 5/0095* (2013.01); *A61B 8/469* (2013.01); *A61B 8/5292* (2013.01); *A61B 8/54* (2013.01)

(58) Field of Classification Search
CPC .... A61B 8/00; A61B 8/08; A61B 8/13; A61B 8/145; A61B 8/5207; A61B 5/0095
See application file for complete search history.

(56) References Cited

U.S. PATENT DOCUMENTS

| | | | |
|---|---|---|---|
| 5,840,023 A | 11/1998 | Oraevsky et al. | 600/407 |
| 2008/0269607 A1* | 10/2008 | Ishida et al. | 600/439 |
| 2009/0036775 A1* | 2/2009 | Ikuma et al. | 600/443 |
| 2010/0217125 A1* | 8/2010 | Kadokura et al. | 600/443 |
| 2011/0257561 A1* | 10/2011 | Gertner et al. | 601/2 |
| 2013/0116536 A1 | 5/2013 | Sato | 600/407 |

FOREIGN PATENT DOCUMENTS

JP       2006-000185       1/2006

* cited by examiner

*Primary Examiner* — James Kish
(74) *Attorney, Agent, or Firm* — Fitzpatrick, Cella, Harper & Scinto

(57) ABSTRACT

Provided is an acoustic wave measuring apparatus including: an acoustic probe; region-of-interest setting unit for setting two or more regions of interest for an object; priority setting unit for setting priorities on the regions of interest; region calculating unit for determining, for each of the set priorities, an inclusion region including the regions of interest set with the priority; scanning method determining unit for assigning a scanning stripe to each of the inclusion regions so as to include all regions of interest included in the inclusion region; scanning path identifying unit for determining a scanning order of a plurality of scanning stripes having a same priority so as to shorten a movement distance of the acoustic probe; and scanning unit for scanning the scanning stripes according to the determined scanning order, based on the priority order, by moving the acoustic probe.

10 Claims, 11 Drawing Sheets

ACOUSTIC WAVE MEASURING APPARATUS AND CONTROL METHOD OF ACOUSTIC WAVE MEASURING APPARATUS

BACKGROUND OF THE INVENTION

Field of the Invention

The present invention relates to an acoustic wave measuring apparatus and a control method of such an acoustic wave measuring apparatus.

Description of the Related Art

An ultrasound measuring apparatus of imaging the structure inside a biological object by transmitting ultrasound waves to the biological object and analyzing the reflected ultrasound waves has been put into practical application in the medical area. When ultrasound waves are transmitted to the biological object, the reflection of ultrasound waves occurs at the interfaces in the biological object having different acoustic impedances. An ultrasound measuring apparatus images configuration information in the biological object by analyzing the reflected waves and detecting the interfaces.

Moreover, in recent years, technology has been devised for analyzing the structure and condition of the surface and inside of a biological object by irradiating a laser beam onto the biological object and generating acoustic waves (photoacoustic waves) caused by such laser irradiation from the inside of the biological object, and analyzing such photoacoustic waves (U.S. Pat. No. 5,840,023). This technology is also referred to as photoacoustic wave measurement, and there is consideration for diverting this technology to medical use, such as for the examination of the inside of the human body, since examination can be performed non-invasively.

Both of the apparatuses described above use an acoustic probe for receiving the ultrasound waves. As the acoustic probe, there are types which are handheld and used by being manually pressed against the skin near the region of interest which the user wishes to acquire information, and types which mechanically scan the surface of the skin of the biological object by introducing a mechanical scanning mechanism.

With existing acoustic probes, it is difficult to produce a sensor with a large opening as with an X-ray imaging apparatus from the perspective of production yield and cost. Thus, the generally adopted method is to use an acoustic probe of a size that is smaller than the region that needs to be examined and covering such region to be examined via automatic or manual scanning.

A measuring apparatus which mechanically drives an acoustic probe includes an input setting unit to be used by the user for setting the region of interest. The input setting unit is configured, for example, from devices such as a keyboard, a mouse, or a touch pen, and is used for setting the region of interest by inputting the detailed measurement setting, or designating the measuring position. Among the foregoing apparatuses, there are types which enable the user to designate, in detail, the scanning track of the probe by using a touch pen or the like (Japanese Patent Application Laid-Open No. 2006-000185). A measuring apparatus performs measurement while moving the acoustic probe so as to trace the designated scanning track.

Patent Literature 1: U.S. Pat. No. 5,840,023
Patent Literature 2: Japanese Patent Application Laid-Open No. 2006-000185

SUMMARY OF THE INVENTION

A conventional measuring apparatus has a problem in that much time is required for measuring an object in both photoacoustic measurement and ultrasound measurement. For example, with mammography for examining breast cancer, the suspected site is compressed and fixed for measurement, and the time that imposes burden on the subject due to compression is preferably short.

In fact, the level of burden felt in response to the compression and fixation will vary among different individuals, and certain subjects are unable to withstand such compression and fixation for a long period of time. Generally speaking, in measurement using ultrasound waves and photoacoustic waves, higher examination accuracy can be obtained as the thickness of the suspected site is shallower. Thus, in order to ensure the required examination accuracy, a certain level of compressive holding is required.

Due to the foregoing circumstances, the measurement time is desirably as short as possible. Nevertheless, when there are a plurality of set regions of interest, the acoustic probe makes a round by scanning all regions and, therefore, the movement distance increases, and there is a problem in that wasted time results depending on the scanning order.

Moreover, even in cases where the measurement is suspended midway, data of a location of high measurement priority is preferably acquired as much as possible. When a plurality of regions of interest are designated, it is possible to deal with the foregoing case by assigning a priority to each of the plurality of regions of interest and performing scanning in that priority order. Nevertheless, for a conventional apparatus to deal with the foregoing problem, the user was required to personally be aware of the foregoing circumstances and designate the scanning track in order from the location of highest priority, and the operation was complicated.

The present invention was devised in view of the foregoing problems, and an object of this invention is to provide an acoustic wave measuring apparatus capable of simplifying the setting operation to be performed by the user, and determining a scanning path among a plurality of regions of interest according to a priority order.

In order to achieve the foregoing object, the present invention provides an acoustic wave measuring apparatus, comprising:

an acoustic probe;

a region-of-interest setting unit configured to set two or more regions of interest for an object;

a priority setting unit configured to set priorities on the regions of interest that have been set;

a region calculating unit configured to determine, for each of the set priorities, an inclusion region including the regions of interest set with the priority;

a scanning method determining unit configured to assign a scanning stripe, which is a rectangle that is formed by moving the acoustic probe in a scanning direction, to each of the inclusion regions so as to include all regions of interest included in the inclusion region;

a scanning path identifying unit configured to determine a scanning order of a plurality of scanning stripes having a same priority so as to shorten a movement distance of the acoustic probe; and a scanning unit configured to scan the scanning stripes according to the determined scanning order, based on the priority order, by moving the acoustic probe.

The present invention also provides a method of controlling an acoustic wave measuring apparatus having an acoustic probe, comprising the steps of:

receiving a designation of two or more regions of interest for an object;

receiving a designation of priorities on the regions of interest that have been set;

determining, for each of the designated priorities, an inclusion region including the regions of interest;

assigning a scanning stripe, which is a rectangle that is formed by moving the acoustic probe in a scanning direction, to each of the inclusion regions so as to include all regions of interest included in the inclusion region; and determining a scanning order of a plurality of scanning stripes having a same priority so as to shorten a movement distance of the acoustic probe, wherein the scanning stripes are scanned according to the determined scanning order, based on the priority order, by moving the acoustic probe.

According to the present invention, it is possible to provide an acoustic wave measuring apparatus capable of simplifying the setting operation to be performed by the user, and determining a scanning path among a plurality of regions of interest according to a priority order.

Further features of the present invention will become apparent from the following description of exemplary embodiments with reference to the attached drawings.

BRIEF DESCRIPTION OF THE DRAWINGS

FIGS. 10A and 10B are schematic diagrams of the overlapping region of the regions of interest and cumulative data according to the second embodiment.

DESCRIPTION OF THE EMBODIMENTS

Embodiments of the present invention are now explained in further detail with reference to the drawings. Note that, as a general rule, the same reference number is given to the same constituent elements and the explanation thereof is omitted.

(System Configuration)

Figure 1:
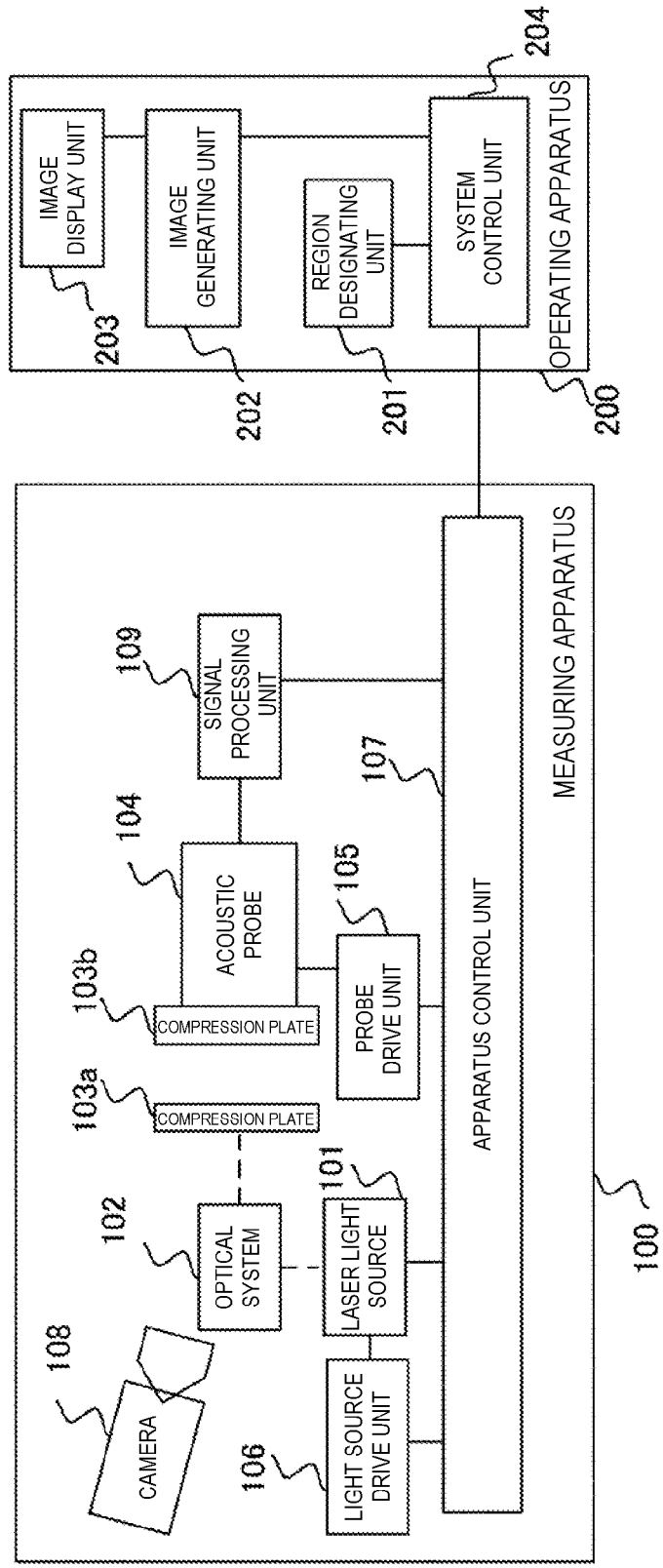
FIG. 1 is a system configuration diagram of the photoacoustic measuring apparatus according to an embodiment of the present invention.

Foremost, the configuration of an acoustic wave measuring apparatus to which the present invention can be applied is explained taking a photoacoustic measuring apparatus as an example with reference to FIG. 1, which is a system configuration diagram. The photoacoustic measuring apparatus according to an embodiment of the present invention is a photoacoustic imaging apparatus for acquiring information (in particular imaging) inside the object. The photoacoustic measuring apparatus enables the imaging of information of a biological object as the object for the diagnosis of malignant tumors and vascular diseases or the follow-up of chemical treatment. Information of a biological object refers to the generation source distribution of the acoustic waves that were generated based on the irradiation of light, and shows the initial sound pressure distribution in the biological object or the light energy absorption density distribution derived therefrom.

The photoacoustic measuring apparatus according to an embodiment of the present invention is configured, in a broad sense, from a measuring apparatus 100 and an operating apparatus 200. The measuring apparatus 100 is an apparatus for performing measurement using photoacoustic waves, and the operating apparatus 200 is an apparatus for operating the measuring apparatus 100. The measuring apparatus 100 includes a laser light source 101, an optical system 102 and a light source drive unit 106, compression plates 103a and 103b, an acoustic probe 104 and a probe drive unit 105, an apparatus control unit 107, a camera 108, and a signal processing unit 109. Moreover, the operating apparatus 200 includes a region designating unit 201, an image generating unit 202, an image display unit 203, and a system control unit 204. The object measuring method is now explained while explaining the configuration of the respective components.

An object (not shown) such as a biological object is fixed by compression plates 103a, 103b for compressing and fixing the suspected site from either side thereof. Note that, when it is not necessary to differentiate the compression plates 103a and 103b, a collective designation of "compression plate 103" will be used. The laser light source 101 is means for generating a laser beam to be irradiated onto the object, and can be moved planarly in a two-dimensional direction by the light source drive unit 106, which is drive means. The laser beam generated by the laser light source 101 is guided to the surface of the compression plate 103a by the optical system 102 such as a lens, a mirror, or an optical fibre, becomes dispersed pulsed light, and irradiated on the object.

When a part of the energy of light that propagated inside the object is absorbed by a light absorber such as blood vessels, acoustic waves are generated based on thermal expansion from that light absorber. Acoustic waves are typically ultrasound waves, and include those which are referred to as sound waves, ultrasound waves, acoustic waves, photoacoustic waves, and light-induced ultrasound waves. In other words, the temperature of the light absorber increases pursuant to the absorption of the pulsed light, volume expansion occurs due to such temperature rise, whereby acoustic waves are generated.

This phenomenon is generally referred to as the photoacoustic effect, and it is possible to acquire the generation source distribution of acoustic waves that were generated based on the irradiation of light, initial sound pressure distribution in the object, or light energy absorption density distribution or absorption coefficient distribution derived from the initial sound pressure distribution, and concentration distribution of the substance configuring the tissues. The concentration distribution of a substance is, for example, oxygen saturation distribution and oxygenated and deoxygenated hemoglobin concentration distribution.

The acoustic probe 104 for detecting acoustic waves corresponds to a detector configured from a plurality of receiving elements which detect the acoustic waves that were generated in or reflected from the object. A detector detects acoustic waves that were generated in the object, and converts the acoustic waves into an electric signal, which is an analog signal. The detection signal acquired by the detector is referred to as a photoacoustic signal. The acoustic probe 104 can also move planarly in a two-dimensional direction by the probe drive unit 105, which is a drive mechanism.

Note that, while an embodiment of the present invention acquires information of an object by using photoacoustic waves, it is also possible to acquire object information by internally providing an ultrasound source in the acoustic probe 104 for transmitting ultrasound waves to the object, and receiving the ultrasound waves that were reflected inside the object. In the foregoing case, the acquired object information refers to information which reflects the difference in the acoustic impedances of the tissues inside the object.

The signal processing unit 109 is means for acquiring internal information of the object from the photoacoustic signal. The photoacoustic signal acquired from the acoustic probe 104 is amplified by a reception amplifier, and converted into a digital signal by an A/D converter. The digital signal is communicated to the operating apparatus 200 via a communication line, operated into three-dimensional information based on image reconfiguration processing, and thereafter displayed as image information on the image display unit 203.

With an embodiment of the present invention, in addition to the above, provided are region of interest designating means (not shown) for the user to designate the region of interest, a camera 108 for providing an observed image of the object to be referred to upon designating the region of interest for the object, and an apparatus control unit 107 for controlling the operation of the measuring apparatus 100. The laser light source 101, the optical system 102, the compression plate 103, the acoustic probe 104, the camera 108, and the region designating unit 201 are now explained in further detail.

<Laser Light Source 101>

When the object is a biological object, irradiated from the light source is light of a specific wavelength that is absorbed by a specific component among the components configuring the biological object. As the light source, preferably used is a pulsed light source capable of generating pulsed light of several nanoseconds to several hundred nanoseconds, and at least one pulse sound source capable of generating pulsed light of 5 nanoseconds to 50 nanoseconds is provided. While laser is preferable as the light source, a light-emitting diode or the like may also be used in substitute for a laser. As the laser, solid-state laser, gas laser, dye laser, semiconductor laser and other lasers may be used.

Moreover, light may also be irradiated from the acoustic probe side, or irradiated from the side that is opposite to the acoustic probe. In addition, light may also be irradiated from either side of the object. Moreover, in this embodiment, while a single light source is shown as an example, a plurality of light sources may also be used. In the case of using a plurality of light sources, a plurality of light sources that oscillate the same wavelength may be used in order to increase the irradiation intensity of the light to be irradiated on the biological object, or a plurality of light sources having a different oscillation wavelength may be used in order to measure the difference in the wavelength of optical characteristic value distribution. Note that, as the light source, if it is possible to use dyes or OPO (Optical Parametric Oscillators) capable of converting the oscillation wavelength, it is also possible to measure the difference in the wavelength of optical characteristic value distribution.

Light shows electromagnetic waves including visible light and infrared light, and specifically light of a region between 500 nm and 1300 nm, preferably light of a region of 700 nm to 1100 nm with low absorption in the biological object, is used. However, when obtaining the optical characteristic value distribution of the biological object tissue which is relatively near the biological object surface, a wavelength region that is broader than the foregoing wavelength region; for instance, a wavelength region of 400 nm to 1600 nm may also be used. Of the light within the foregoing range, a specific wavelength may be selected based on the components to be measured.

Moreover, with a laser light source, the irradiation frequency is usually determined in advance. The irradiation frequency is preferably high as possible since the irradiation frequency affects the number of photoacoustic measurements that can be performed per unit time. In this embodiment, the irradiation frequency of the laser light source is 10 Hz.

<Optical System 102>

The optical system 102 is, for example, a mirror which reflects light, a lens which focuses, expands or changes the shape of light, a prism which disperses, refracts and reflects light, an optical fibre which propagates light, a diffuser panel, or the like. Light that is irradiated from the light source can be guided to an object by using an optical member such as a lens or a mirror, or propagated by using an optical member such as an optical fibre. The foregoing optical members may be of any type so as long as the light emitted from the light source can be irradiated, in the intended shape, onto the object.

Note that, generally speaking, rather than focusing the light with a lens, it is more preferable to broaden the area to a certain extent from the perspective that the diagnosis region can be expanded. Moreover, the region where light is irradiated onto the object (hereinafter referred to as the "irradiation region") is preferably movable. By causing the irradiation region to be movable, light can be irradiated to a broader range. Moreover, preferably, the irradiation region can be moved in synch with the acoustic probe 104. As the method of moving the irradiation region, a method of using a movable mirror or a method of mechanically moving the light source itself may be adopted.

<Compression Plate 103>

The compression plate 103 retains at least a part of the shape of the object to be constant, and is provided between the object and the acoustic probe 104. When the object is sandwiched from either side using the compression plates, the position during measurement is fixed, and it is thereby possible to reduce the positional errors caused by body motion or the like. Moreover, by compressing the object, light can efficiently reach the deep part of the object. As the holding member, preferably used is a member having high optical transmittance and high acoustic compatibility with the object and the acoustic probe. In order to improve the acoustic compatibility, an acoustic matching member such as a gel may be interposed between the compression plate and the object, and between the compression plate and the acoustic probe.

<Acoustic Probe 104>

The acoustic probe 104 is a device which detects acoustic waves and converts the detected acoustic waves into an electric signal. The photoacoustic waves generated from a biological object are ultrasound waves of 100 kHz to 100 MHz. Thus, as the acoustic probe 104, an ultrasound detector capable of receiving the foregoing frequency band is used. Note that any detector may be used so as long as it is able to detect the acoustic wave signal and convert the acoustic wave signal into an electric signal; for instance, a transducer that uses the piezoelectric phenomenon, a transducer that uses the oscillation of light, or a transducer that uses the change in capacity. Note that a detector is preferably configured by a plurality of receiving elements being arrayed two-dimensionally.

As a result of using such two-dimensional arrayed elements, acoustic waves can be simultaneously detected at a plurality of locations, and it is possible to shorten the detection time as well as reduce the influence of vibration of the object and so on. In an embodiment of the present invention, let it be assumed that the receiving element pitch is a 2 mm interval, the receiving element array is five elements in the main scanning direction (direction in which the acoustic probe moves while performing the scan), and five elements in the sub scanning direction (direction that is orthogonal to the main scanning direction).

<Camera 108>

The photoacoustic measuring apparatus according to an embodiment of the present invention includes a camera 108 for providing images to be referred to by the user upon designing the regions of interest to be subject to photoacoustic measurement. The camera 108 is installed in a direction that is orthogonal to the holding plates that compress and hold the object, and the captured image is transmitted to the operating apparatus 200, and displayed as the observed image. The visual field of the camera is preferably installed at a view angle in which the photoacoustic measurable range can be viewed. The camera is installed so that the compressed and held object can be observed, and the user can designate the region of interest while observing the compressed and held object.

<Region Designating Unit 201>

The photoacoustic apparatus according to an embodiment of the present invention includes a region designating unit 201 as means for the user to designate the region of interest to be imaged. The user designates the region for imaging the region of interest by using input means such as a mouse while referring to the observed image of the compressed and held object that is displayed on the display device. The input means is not limited to a mouse or a keyboard, and may also be a tablet type or a touch pad mounted on the display device surface. In this embodiment, a plurality of regions of interest can be designated.

In an embodiment of the present invention, in order to associate the observed image and the scanning surface of the acoustic probe, the camera 108 is installed so as to capture the observed image of a surface that is parallel to the plane to be scanned by the acoustic probe relative to the object. The user can designate the region to be scanned with the probe by setting a two-dimensional rectangle (measurement designated region) at a location corresponding to the position to be measured while referring to the observed image captured by the camera. Note that the measurement designated region may also be a shape other than a rectangle.

As the method of designating the measurement region, coordinates may also be designated based on input using a keyboard. The coordinate designating method in the foregoing case may be the designation of central coordinates of the measurement region of a predetermined size in order to specify the measurement region, or a plurality of vertex coordinates may be designated on the reference image plane so as to set the measurement designated region. In all of the foregoing cases, it is possible to set a measurement designated region as the two-dimensional rectangular region on the reference image plane.

The photoacoustic measuring apparatus according to an embodiment of the present invention converts the image coordinate system of the camera into an apparatus coordinate system based on the designated measurement designated region, and performs control so as to move the probe to a corresponding position of the actual object.

Figure 2:
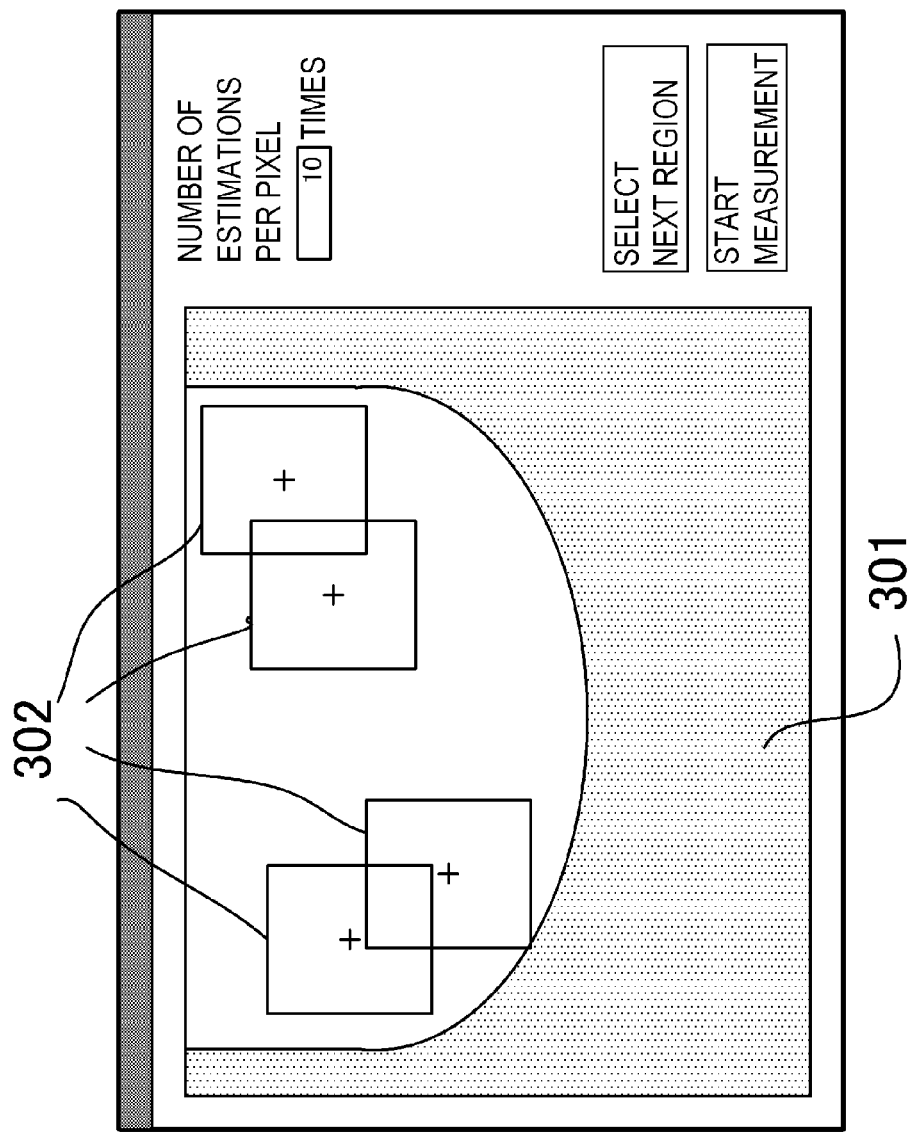
FIG. 2 is a setting screen example of the region of interest by the region designating unit.

The screen image for designating the region in this embodiment is shown in FIG. 2. In the diagram, 301 represents an observed image from a specific direction relative to the object, and 302 represents a measurement designated region that was designated by the user while referring to the observed image. With respect to the measurement designated region 302, it is possible to designate a region of an arbitrary size through operations such as disposing a rectangle of a pre-set size, or inputting a rectangle using a pointing device.

Moreover, a function for designating a plurality of measurement designated regions is also provided. For example, this is a method where a multiple selection button is provided and, when the measurement designated region is designated while pressing the multiple selection button, a plurality of measurement designated regions which were selected while the multiple selection button is being pressed are stored. As another method, by providing a "Select next region" menu on the menu screen and designating this menu each time a measurement designated region is designated, the region of interest can be designated successively. In all of the foregoing methods, it is preferable to prepare means for cancelling a part or all of the designations of the measurement designated region.

Moreover, in an embodiment of the present invention, after setting a plurality of measurement designated regions, it is possible to newly select the respective measurement designated regions using a pointing device and individually designate the scanning priority. In the foregoing case, the same scanning priority may be designated in a plurality of regions, or higher scanning priority may be set in the order that the measurement designated region was set.

The foregoing processes are executed by the region designating unit 201 and the system control unit 204, and correspond to the region-of-interest setting unit and the priority setting unit in the acoustic wave measuring apparatus to which the present invention can be applied.

First Embodiment

The operation of the photoacoustic measuring apparatus according to the first embodiment is now explained in detail with reference to the drawings.

<Designation of Region of Interest>

Figure 4:
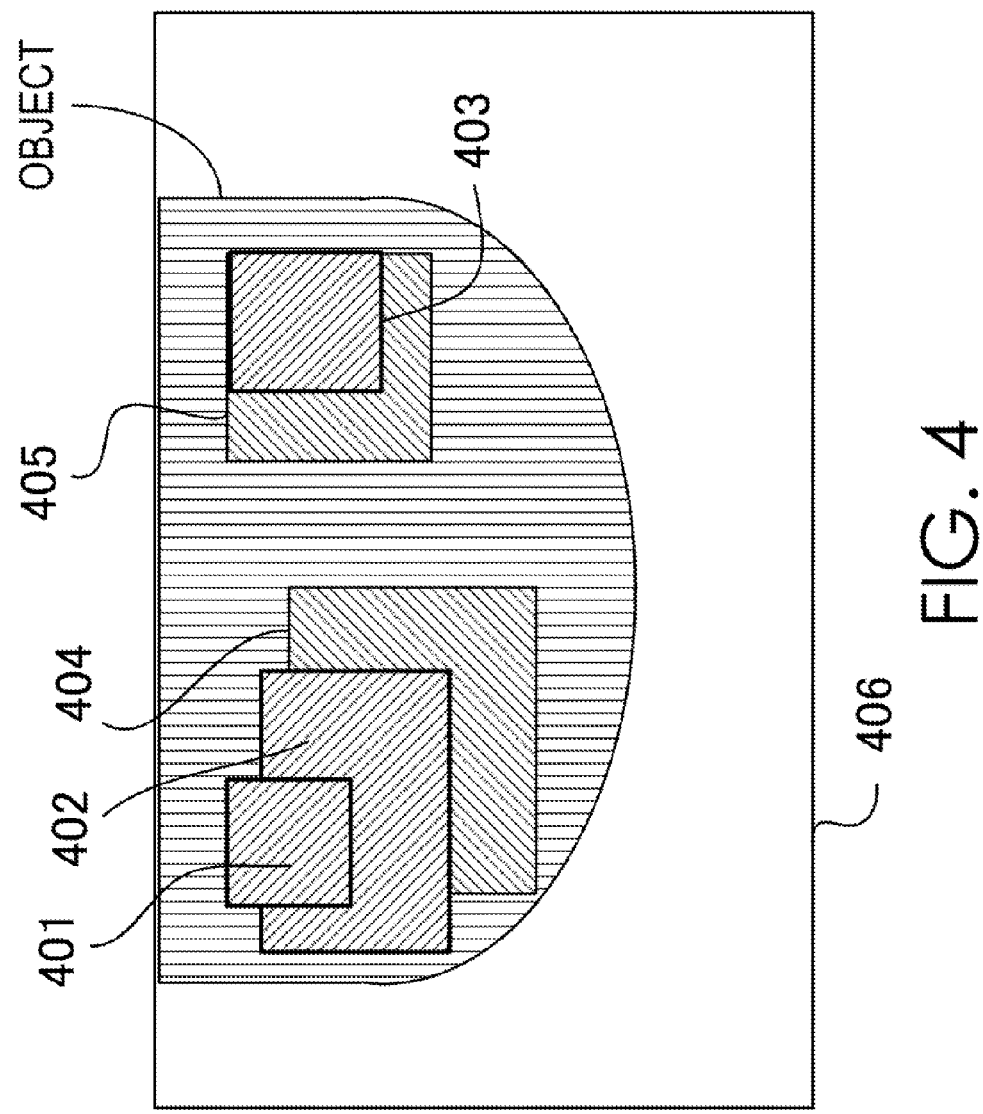
FIG. 4 is a schematic diagram in the case of setting a plurality of regions of interest.

A plurality of measurement designated regions, so called regions of interest, are designated by a user via the region designating unit 201. A specific example of the designation of the measurement designated region by the user is shown in FIG. 4. In the diagram, 406 represents a region corresponding to the observed image, and is a planar range in which the acoustic probe can perform scanning. 401 to 405 are measurement designated regions that were designated by the user. 401 to 403 are regions which are set with a high priority (let this be priority 1), and 404, 405 are regions which are set with a low priority (let this be priority 2). As shown in the diagram, regardless of the setting of priority, it is also possible to designate the measurement designated regions in a mutually overlapping state. The designated regions of interest are stored in the system control unit 204.

Moreover, in the foregoing case, the measuring conditions of the photoacoustic measurement can also be set. In this embodiment, it is also possible to set the number of acquisitions (cumulative number) of the photoacoustic data in the same coordinate position upon measuring the measurement region. Here, let it be assumed that the cumulative number is set to 10 times.

Figure 3:
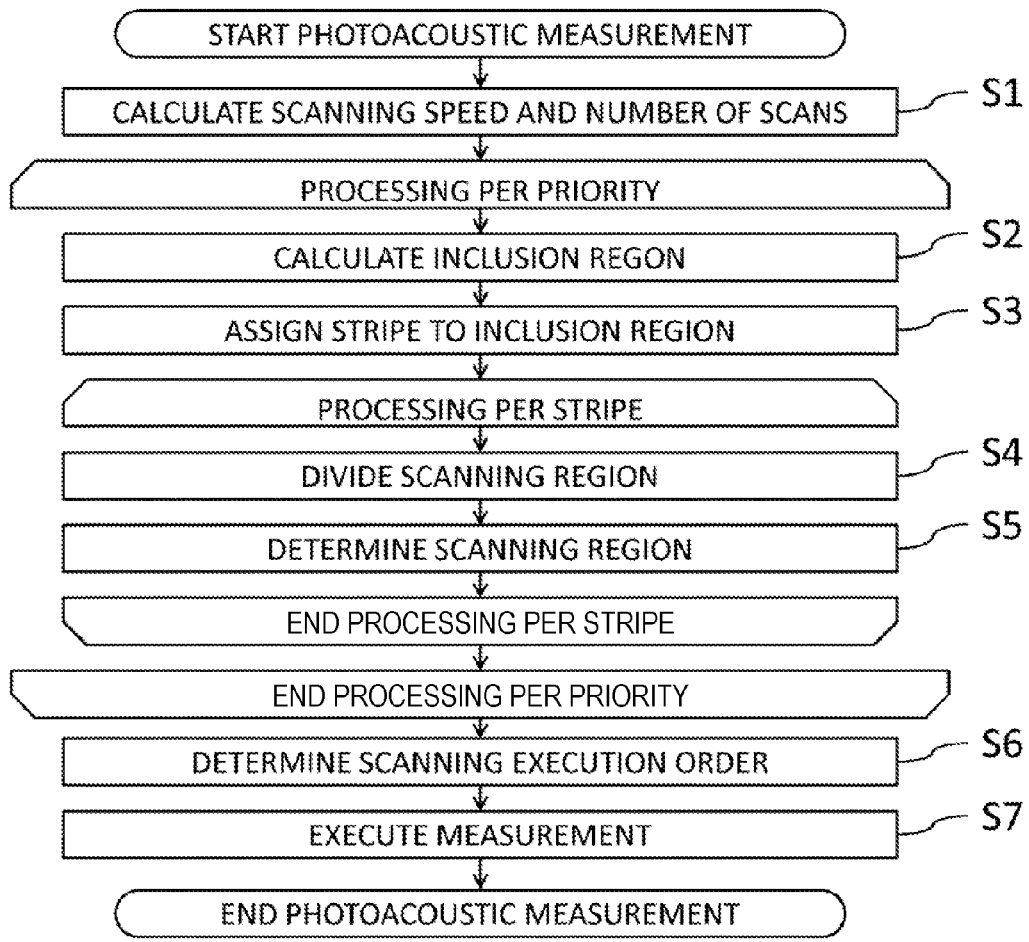
FIG. 3 is a processing flowchart of the controller unit according to the first embodiment.

When the user gives instructions for starting measurement, a measurement request message is sent from the system control unit 204 to the apparatus control unit 107. The processing contents of the measuring apparatus 100 in this embodiment are now explained with reference to FIG. 3, which is a processing flowchart of the controller unit 107.

<Calculation of Scanning Speed for Measurement>

When the apparatus control unit 107 receives a measurement request message, the apparatus control unit 107 foremost calculates the scanning speed for measurement and the number of scans required for obtaining the cumulative number desired by the user (S1). Let it be assumed that the number of elements of the acoustic probe in the main scanning direction is Enx elements, the element pitch is Ep (mm), the cumulative number of photoacoustic measurement is Mn, and the light-emitting frequency of the laser light source is LHz (Hz). In order to simplify the explanation, when the cumulative number Mn is a multiple of the number of elements Enx, the scanning speed Vx (mm/sec) of the acoustic probe and the laser light source in the main scanning direction and the number of scans Sn are calculated based on Formula (1) and Formula (2), respectively. The processing of step S1 corresponds to the moving speed acquiring unit in the acoustic wave measuring apparatus to which the present invention can be applied.

$$Vx = Ep \times LHz \quad (1)$$

$$Sn = Mn/Enx \quad (2)$$

In the case of this embodiment, since the number of elements of the acoustic probe 104 in the scanning direction is five elements, estimation can be performed 5 times when the acoustic probe 104 is to be moved on the object surface, and 10 estimations can be performed if the acoustic probe makes one full round. Moreover, since the element pitch is 2 mm and the light-emitting frequency of the laser light source is 10 Hz, the scanning speed upon measurement will be 20 mm/sec.

The foregoing calculation example of the scanning speed is an example of a case using photoacoustic measurement. Upon applying an acoustic wave measuring apparatus of a type which transmits ultrasound waves to an object and receives reflected waves thereof, the moving speed upon measurement can be similarly calculated based on the drive frequency of the acoustic probe and the element pitch of the acoustic probe in the main scanning direction.

The scanning speed and number of scans for measurement obtained as described above are used for calculating the scanning region or determining the measurement order explained later.

<Calculation of Scanning Region>

Subsequently, the apparatus control unit 107 calculates the scanning region as the region in which the acoustic probe actually performs scanning. Calculation of the scanning region is performed in the scanning priority order from the measurement designated region having a high scanning priority. Foremost, among the plurality of measurement designated regions that were designated, the inclusion region which includes all measurement designated regions of the scanning priority to be focused is calculated (S2). In other words, a region which includes all of the measurement designated regions and which is the smallest rectangular region is obtained as the inclusion region. The scanning priority is hereafter simply referred to as the "priority".

Figure 5:
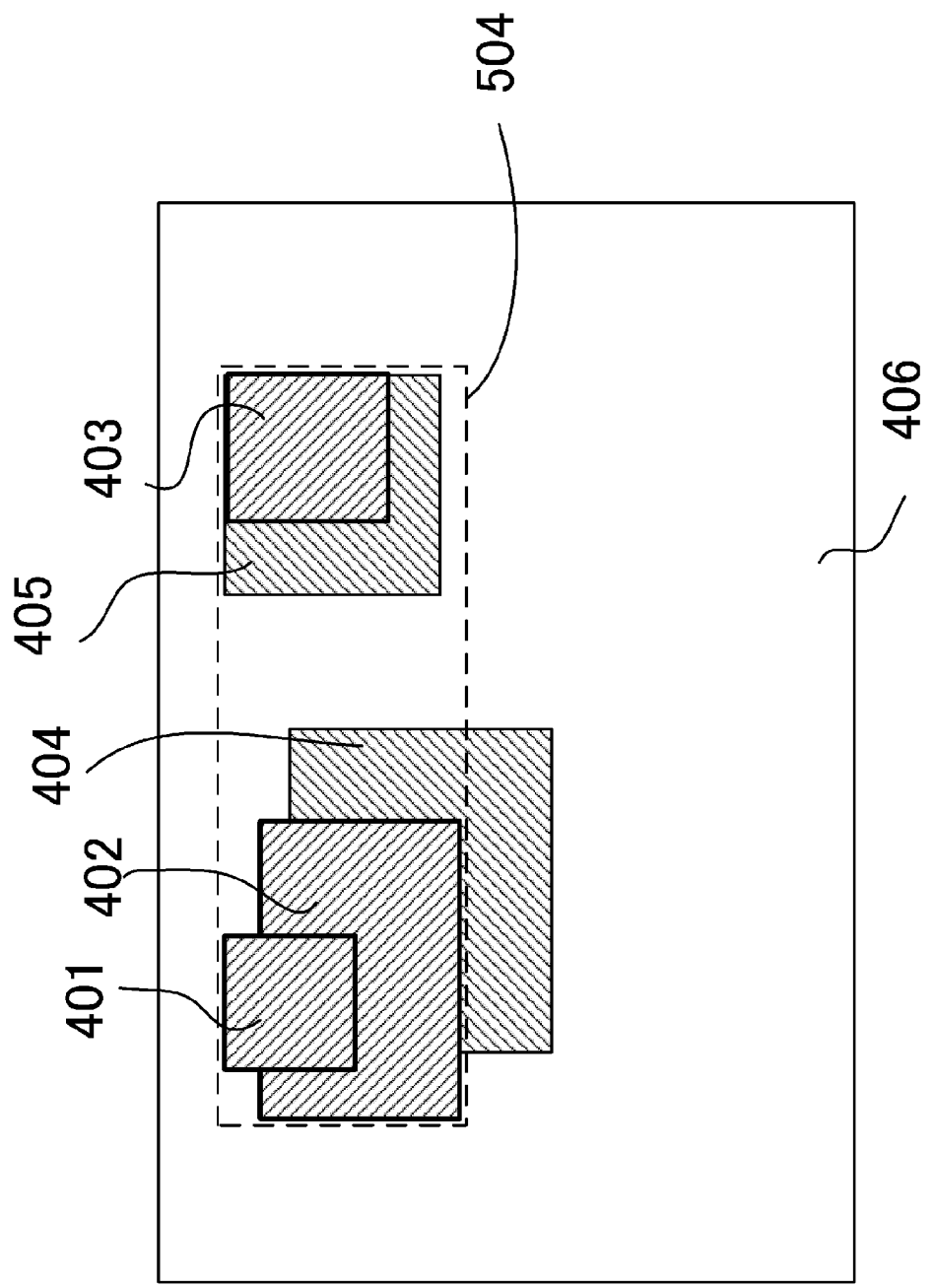
FIG. 5 is a schematic diagram of the inclusion region relative to the region of interest according to the first embodiment.

FIG. 5 shows an image of the inclusion region of priority 1. Regions 401, 402, 403 shown in FIG. 5 are the measurement designated regions of priority 1, and a rectangle 504 is the inclusion region that was calculated from the measurement designated regions.

Subsequently, a scanning strip is assigned to the inside of the inclusion region of priority 1 (S3). A scanning stripe refers to a rectangular region capable of moving the acoustic probe and the light source (hereinafter collectively referred to as the "measurement system") in the main scanning direction. In this embodiment, the width of the scanning stripe in the main scanning direction in the scanning plane of the acoustic probe becomes the length of scanning and measurement that were performed by the acoustic probe, and the width in the sub scanning direction becomes the length of all element regions of the acoustic probe in the sub scanning direction. The scanning stripe is hereinafter simply referred to as the "stripe".

In reality, while the region subject to photoacoustic measurement is a three-dimensional region including the depth direction, unless separately provided for herein, the two-dimensional projection plane on the scanning surface of the measurement system is indicated as a "stripe".

Figure 6:
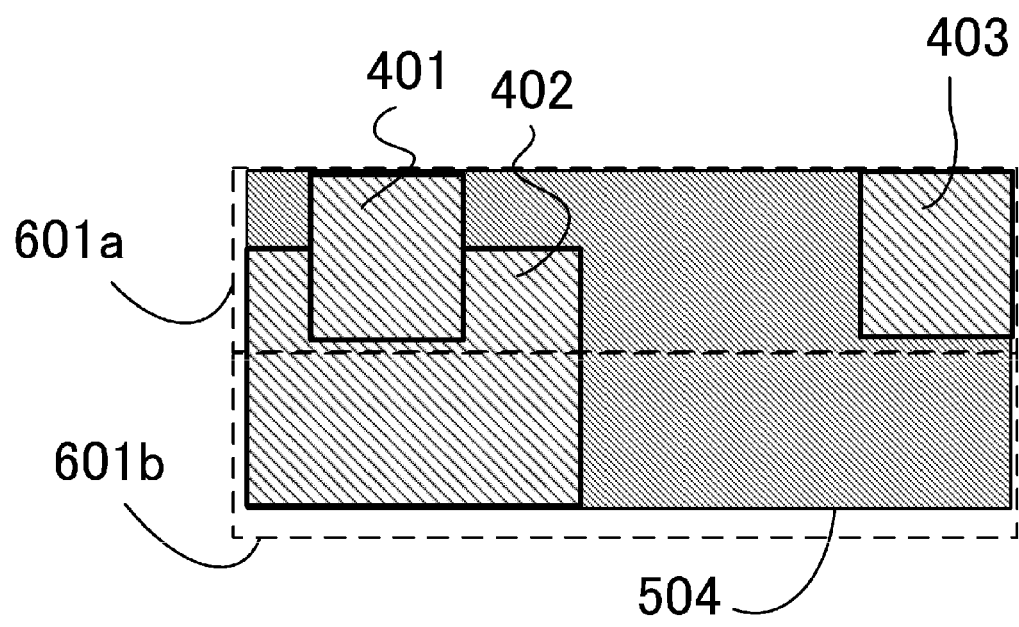
FIG. 6 is an example of the stripe assignment to the inclusion region according to the first embodiment.

FIG. 6 shows an example of assigning the stripe. Stripes 601a, 601b are respectively stripes that were assigned to the inclusion region 504 set with priority 1. In this embodiment, while the stripes are assigned to the inclusion region 504 in order from the top in a manner of lining the stripes, any method may be used for assigning the stripes so as long as all measurement designated regions can be included in the stripe.

Subsequently, the stripe to be processed (hereinafter referred to as the "notable stripe") is divided into an actual scanning region and a non-scanning region (S4). An actual scanning region is a region where the acoustic probe actually performs scanning for measuring the measurement designated region, and a non-scanning region refers to the other regions. The actual scanning region is a region that includes the measurement designated region among the regions included in the stripe.

Figure 7:
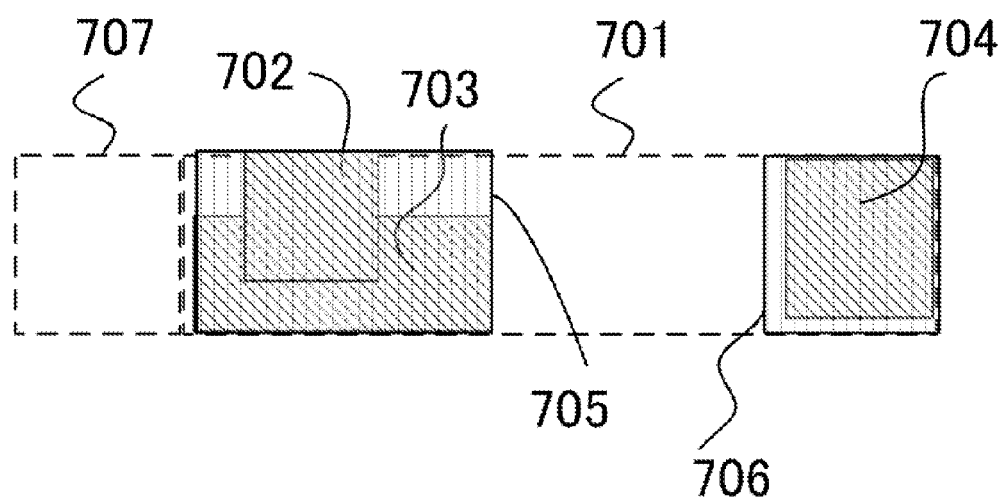
FIG. 7 is a schematic diagram of determining the scanning region in the notable stripe according to the first embodiment.

FIG. 7 shows an example where the notable stripe has been divided. 701 is a notable stripe, and 702, 703, 704 are regions that overlap with the notable stripe 701 among the measurement designated regions 401, 402, 403 having priority 1. 705 and 706 including the foregoing regions are the actual scanning regions, and the intermediate region is the non-scanning region.

Subsequently, the scanning region of the notable stripe is determined (S5). The scanning region determination is the processing of determining whether the divided regions in the stripe are classified as any one of the following three types.

(1) Region (continuous scanning region) subject to photoacoustic measurement as a result of continuously moving (continuously scanning) the measurement system in the main scanning direction while acquiring the acoustic waves.

(2) Region (moving region) in which the measurement system moves but photoacoustic measurement is not performed.

(3) Region (fixed measuring region) that is measured (fixed measuring) by stopping the measurement system.

In step S5, whether the foregoing actual scanning region is to be measured via continuous scanning or measured via repeated fixed measuring is determined. Moreover, with respect to the non-scanning region, whether to move the acoustic probe without performing measurement or perform continuous scanning is determined. Specifically, the scanning method of the respective regions or the moving method is determined so that the time required for the measurement of the notable stripe and movement processing becomes the shortest.

The processing time upon setting a region as the continuous scanning region can be calculated by dividing the scanning distance by the continuous scanning speed Vx. Moreover, the processing time upon setting a region as the fixed measuring region can be calculated by dividing the laser irradiation frequency by the cumulative number. Moreover, the processing time of the moving region can be calculated by dividing the movement distance by the simple moving speed of the drive apparatus. The processing of step S2 corresponds to the region calculating unit in the acoustic wave measuring apparatus to which the present invention can be applied, and the processing of steps S3 to S5 corresponds to the scanning method determining unit.

A specific calculation example of the scanning region determination is now explained with reference to FIG. 7. 707 is the initial position of the acoustic probe.

With this calculation example, let it be assumed that the element pitch of the acoustic probe is 2 mm, the element region of the acoustic probe is a 10 mm square, the scanning speed during measurement is 20 mm/sec, the simple moving speed is 50 mm/sec, the light-emitting frequency of the light source is 10 Hz, and the cumulative number is 5 times. Let it be further assumed that the length of the notable stripe 701 in the main scanning direction is 50 mm, the actual scanning region 705 is 20 mm, and the actual scanning region 706 is 10 mm.

Figure 9:
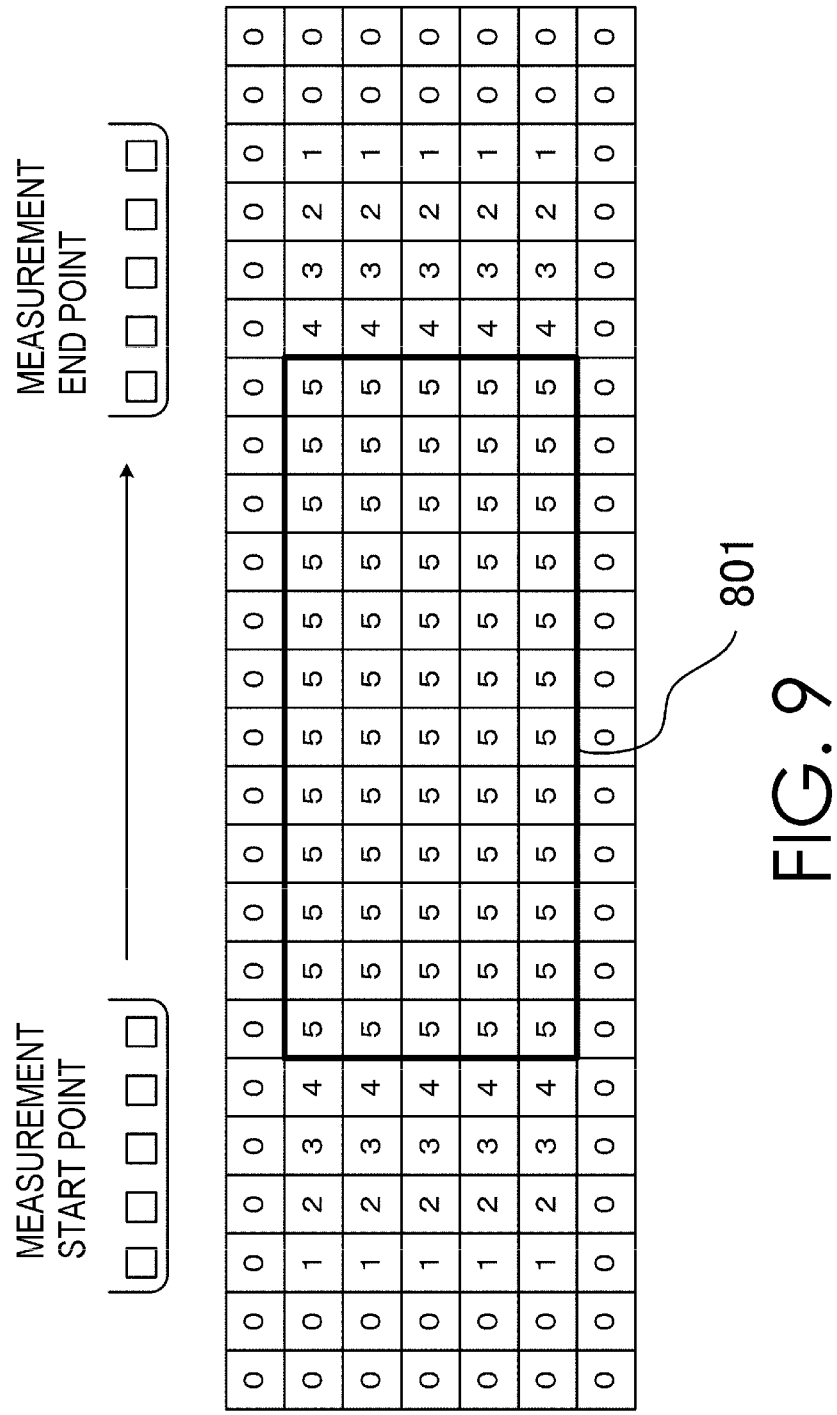
FIG. 9 is a schematic diagram of data accumulation based on the continuous scanning by the acoustic probe.

Note that, when performing continuous scanning, since measurement is performed while moving the acoustic probe, there are cases where the movement distance of the acoustic probe becomes slightly longer than the length of the actual scanning region (refer to FIG. 9). In this embodiment, the scanning distance is calculated by adding a distance (10 mm) for the amount of the element region of the acoustic probe.

Foremost, considered is a case where, after measuring the actual scanning region 705, the acoustic probe is moved short of the actual scanning region 706 by passing through the non-scanning region.

When the actual scanning region 705 is subject to continuous scanning, the distance required for scanning 705 will be 30 mm, and the simple movement distance of the non-scanning region will be 10 mm. Thus, the scanning time will be 30/20=1.5 sec, the moving time will be 10/50=0.2 sec, and the required time can be calculated as 1.7 sec.

Meanwhile, when the actual scanning region 705 is subject to fixed measuring, the simple movement of 10 mm will be performed a total of 4 times, and the measurement requiring 0.5 sec will be performed twice. Thus, the measurement time will be 0.5×2=1 sec, the moving time will be 40/50=0.8 sec, and the required time can be calculated as 1.8 sec. Thus, it can be seen that the measurement of the actual scanning region 705 can be performed quicker via continuous scanning.

Next, considered is a case where, after measuring the actual scanning region 706, the acoustic probe is moved outside the notable stripe.

When the actual scanning region 706 is subject to continuous scanning, the distance required for scanning 706 will be 20 mm, and the required time can be calculated as 1 sec. Meanwhile, when the actual scanning region 706 is subject to fixed measuring, the simple movement of 10 mm will be performed a total of twice, and the measurement requiring 0.5 sec will be performed once. Thus, the measurement time will be 0.5 sec, the moving time will be 20/50=0.4 sec, and the required time can be calculated as 0.9 sec. Thus, it can be seen that the measurement of the actual scanning region 706 can be performed quicker via fixed measuring.

In other words, it can be seen that the scanning can be performed quickest when the actual scanning region 705 is set as a continuous scanning region and the actual scanning region 706 is set as a fixed measuring region. The remaining portion will be the moving region. Note that the foregoing explanation is of a case where scanning is performed once, but the time required for measurement can be obtained with the same logic even in cases where the number of scans is a plurality of times; for instance, performing scanning twice in a full round.

The foregoing process of calculating the scanning region (steps S4 and S5) is repeated for all stripes, and the scanning region calculation of the overall inclusion region is performed.

Moreover, the processing of foregoing steps S2 to S5 is further performed in priority order, and the same scanning region is calculated for each set priority.

<Determination of Scanning Track>

Subsequently, the apparatus control unit 107 determines the scanning order among the actual scanning regions regarding the respective scanning regions that were calculated for each priority (S6). The determination criteria is to determine an order which will shorten the total measurement time of the measurement regions of all priorities, and shorten the displacement of the measurement system. The processing of step S6 corresponds to the scanning path identifying unit in the acoustic wave measuring apparatus to which the present invention can be applied.

Figure 8:
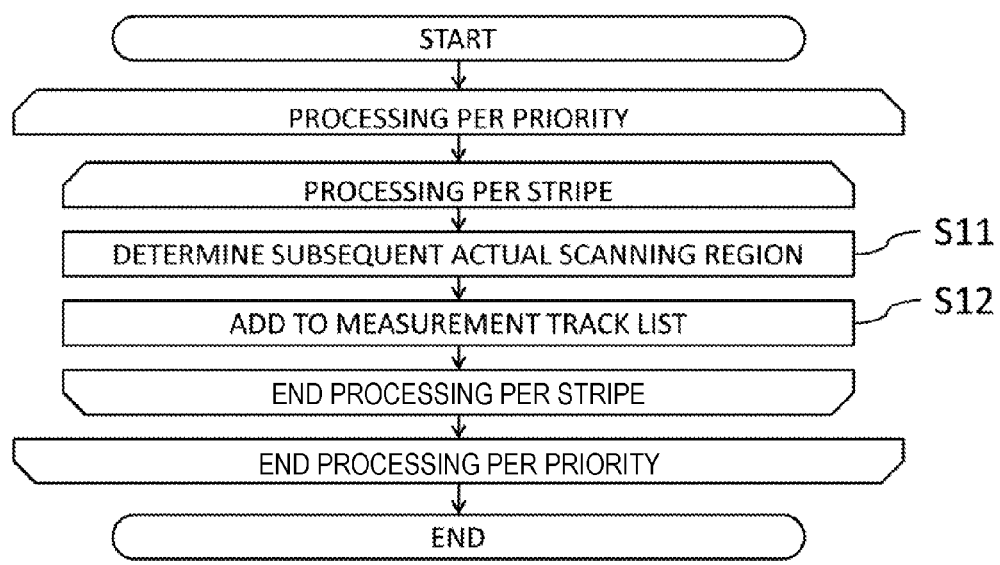
FIG. 8 is a detailed explanatory diagram of the processing flowchart of the controller unit.

The processing of step S6 is explained in further detail in the flowchart of FIG. 8. When step S6 is started, processing of the stripe with the highest priority is started. Foremost, the actual scanning region to be scanned is determined (S11). In the initial processing, the actual scanning region to be scanned is the actual scanning region that is closest to the acoustic probe.

Subsequently, information of the actual scanning region is added to the measuring track list (S12). The measuring track list records, at least, the measurement start coordinates, measurement method (continuous scanning measuring or fixed measuring), and information regarding the scanning distance. Note that, when there are a plurality of actual scanning regions in the same stripe, all actual scanning regions are added to the measuring track list.

When there are unprocessed regions of the same priority, the same processing is performed with the actual scanning region of the closest distance to the measurement end coordinates of the added actual scanning region as the subsequent destination.

When the processing of all stripes of the same priority is complete, the same processing is performed regarding one lower priority. As a result of performing the foregoing processing, information of the actual scanning region to be scanned will be listed in the scanning execution order, and stored for each priority.

The apparatus control unit 107 refers to the measuring track list that was stored according to the foregoing procedure, and executes measurement while moving between the actual scanning regions (S7). The processing of step S7 corresponds to the scanning unit in the acoustic wave measuring apparatus to which the present invention can be applied.

The photoacoustic measuring apparatus according to this embodiment calculates the region to be scanned by the measurement system in the priority order based on the measurement designated region and priority designated by the user, and determines the track on which the measurement system is to move upon performing the photoacoustic measurement. Consequently, the user is no longer required to set the scanning track, and can concentrate on the designation of the region of interest.

Moreover, the photoacoustic measuring apparatus according to this embodiment comprises moving speed acquiring unit for calculating the continuous scanning speed, region calculating unit for determining the time required for the measurement and determining the scanning region, and scanning path identifying unit which uses the movement distance other than measurement as the measuring condition. Consequently, in comparison to a case of performing simple scanning scheduling such as subjecting all regions to continuous scanning, it is possible to efficiently calculate the scannable track, and thereby shorten the measurement time.

Note that the moving speed acquiring unit (step S1) may be omitted if the moving speed and cumulative number are defined there is no need to calculate the same. Moreover, a part of the scanning method determining unit (steps S4 and S5) may also be omitted if there is no need to perform scanning region determination in the same priority. Even with the foregoing configurations, it is possible to scan the plurality of regions of interest in the priority order designated by the user, and additionally yield an effect of being able to shorten the measurement time.

Note that the receiving elements of the acoustic probe are not limited to the grid pattern of this embodiment, and may also be a honeycomb shape, a hound's-tooth shape, or other arrangement. The determination of the moving speed of the probe is not limited to the method illustrated in this embodiment, and various algorithms may be applied for adjusting the scanning speed in dependence of the measuring conditions or apparatus configuration. Moreover, the scanning speed calculation function in this embodiment aims to obtain the probe moving speed for measurement and, therefore, the reference parameters and algorithms are not limited to those described in this embodiment.

Second Embodiment

The second embodiment is the mode of detecting a portion which overlaps with the regions of different priorities and optimizing the shape of the regions in step (S4) of dividing the scanning region shown in the first embodiment. The processing other than step S4 and the system configuration are the same as the first embodiment.

FIG. 9 is a diagram showing the state of data accumulation of the region that was captured while moving the acoustic probe. In the diagram, the observer's right-side direction is the main scanning direction. The checkered rectangle represents the location where the receiving elements of the acoustic probe existed upon performing photoacoustic measurement while shifting the acoustic probe in the main scanning direction one element at a time. In order to perform photoacoustic measurement while shifting the acoustic probe in the main scanning direction one element at a time, the scanning region will be, as shown in the diagram, filled by grids of the element size of the acoustic probe without any space therebetween. Note that, in this embodiment, let it be assumed that the cumulative number has been set to 5 times.

The numbers in the grid show number of times that photoacoustic measurement was performed; that is, the cumulative number of photoacoustic measurement, at that location. A region 801 is the actual scanning region, and a region where estimation is performed 5 times. Since scanning and estimation are performed while shifting the acoustic probe in the main scanning direction one element at a time, this means that there will constantly be four elements' worth of excess data before and after the actual scanning region to be measured.

Figures 10A, 10B:
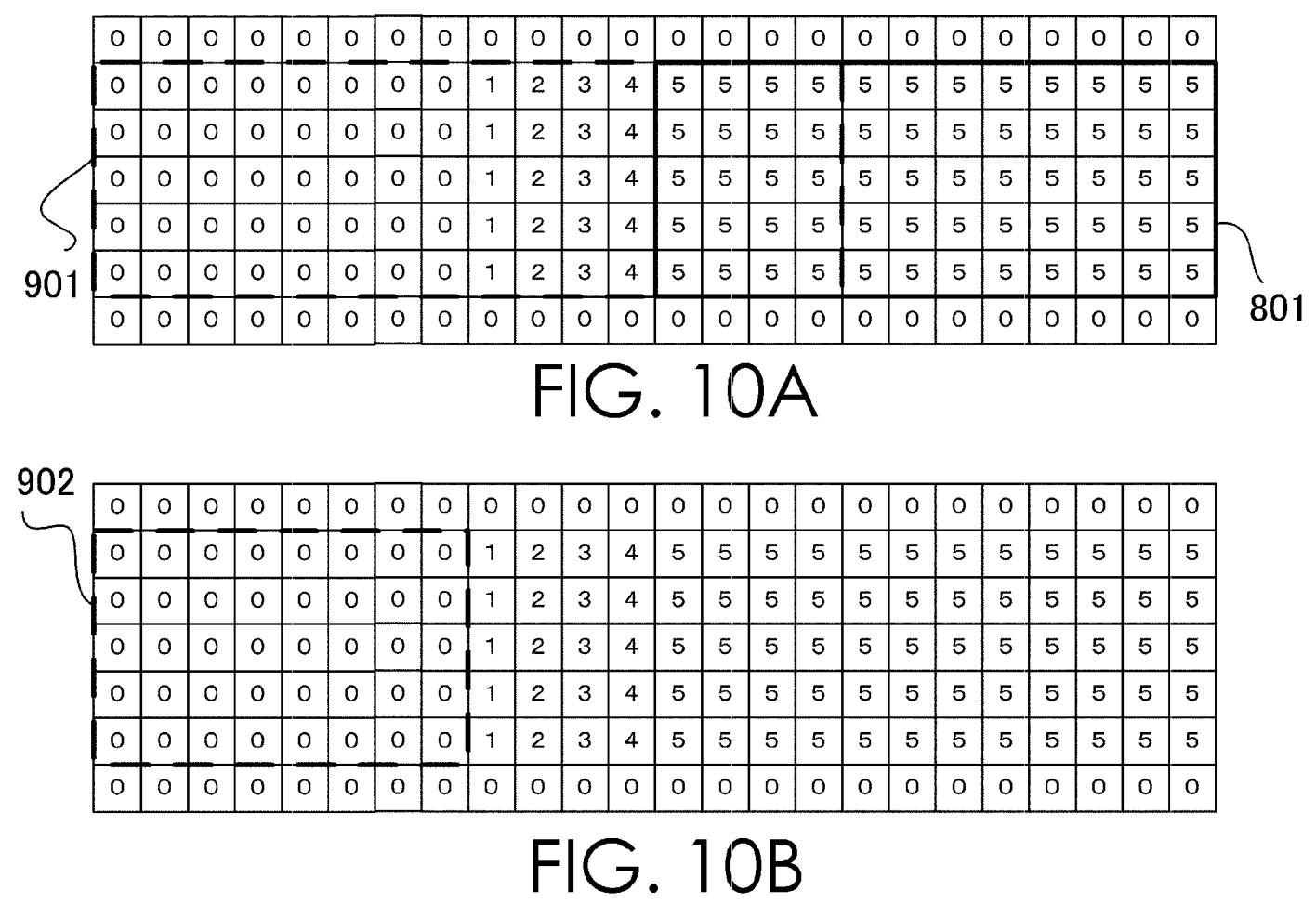

FIG. 10 shows an example of a case where a region of high priority (first priority) and a region of low priority (second priority) overlap with each other. As shown in FIG. 10A, let it be assumed that an unmeasured region 901 of low priority is set so as to overlap with the measured region 801 of high priority. In the foregoing case, as described above, there will be data in which the cumulative number is less than 5 obtained during the measurement of the region 801.

In other words, when actual scanning regions of different priorities overlap respectively, the actual scanning region can be reduced by reusing the data obtained upon scanning the region of high priority for the region of low priority. Specifically, in addition to the regions in which estimation has been performed 5 times, the region may be further reduced in an amount of four elements so as to achieve a region 902 shown in FIG. 10B. When continuous scanning is performed to the region 902, since four elements' worth of data on the right side can be similarly acquired, it is possible to obtain a cumulative number of 5 times for all regions. In other words, it is possible to shorten the measurement time since there is no need to move the distance of the reduced amount of eight elements.

In order to realize the foregoing function, in this embodiment, the photoacoustic wave measuring apparatus according to the first embodiment is additionally equipped with a storage region in which the actual scanning region is further divided based on the element pitch of the acoustic probe, and the cumulative number of each of the divided regions is mapped.

In addition, upon performing the processing of step S4, the scheduled cumulative number associated with the measurement is mapped to each of the divided regions. Upon performing the scheduling of low priority, the portion in which the predetermined number of estimations is complete regarding the determination of the measurement region is excluded from the actual scanning region. Moreover, even when it is less than the predetermined number of times, any region that is overlapping with the previously measured region is determined to be a portion capable of reusing the measured data, and also excluded from the actual scanning region. In other words, the actual scanning region is reduced so as to include only the unmeasured regions.

In normal measurement processing, any region that does not satisfy the cumulative number set in the measuring conditions such as the region outside the region 801; that is, excess data, is erased. Nevertheless, in this embodiment, since all cumulative data is stored for each coordinate until all measurement is complete, it is possible to divert the data upon measuring the actual scanning region of low priority, and thereby improve the measuring efficiency.

Note that, in this embodiment, while a region that has been estimated even once was excluded from the actual scanning region, the determination of exclusion is not limited to the case that was illustrated in this embodiment. For example, the reference cumulative number or the like may also be changed according to the cumulative number of data, probe shape, sensitivity distribution, or the like.

Moreover, while this embodiment determined the overlap of regions in step S4 of dividing the scanning region, this may also be performed in other steps so as long as the processing can exclude the overlap of regions of different priorities. For example, it is also possible to determine the overlap of regions in step S2 of determining the inclusion region per priority.

Third Embodiment

The third embodiment is a mode of changing the assignment method in step (S3) of assigning the stripes to the inclusion region. Upon assigning the stripes to the inclusion region, the stripe arrangement position is adjusted so that measurement of regions of all priorities is completed with the shortest possible scanning distance. Note that the processing other than step S3 and the system configuration are the same as the second embodiment.

With the photoacoustic measuring apparatus according to the first and second embodiments, since the photoacoustic measurement is performed in stripe units, excess regions will be measured when they are smaller than the height of the actual scanning regions in which the measurement designated regions designated by the user. If it is possible to measure the measurement designated region, the excess regions may be located anywhere, and the stripes may be moved in the sub scanning direction in the amount of the width of the excess region.

FIG. 11 is an explanatory diagram of a case where an excess data measurement region occurs. In FIG. 11A, regions 1001 and 1002 are the actual scanning regions designated as being high priority (priority 1), a region 1003 is the actual scanning region designated as being low priority (priority 2). The stripes 1004 and 1005 are stripes that were assigned for measuring the actual scanning regions designated as being priority 1. In the first and second embodiments, the stripe arrangement will be of the illustrated shape since the stripes are assigned, in order from the top, to the inclusion region of each priority.

Figure 11B:
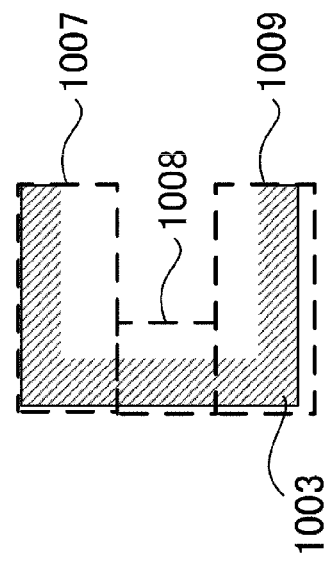
FIG. 11A to 11D are schematic diagrams in a case where an excess data measurement region occurs according to the third embodiment.

When the region 1003 of low priority is to be measured after measuring the regions 1001, 1002, the unmeasured region will be shown as an angular C-shape as shown in FIG. 11B. In other words, in order to measure the entire region 1003 of low priority, it is necessary to newly measure regions 1007 to 1009. Assuming that the horizontal width of the regions 1007, 1009 is 25 mm and the horizontal width of the region 1008 is 10 mm, the distance that needs to be newly measured will be 25+10+25=60 mm.

Figure 11D:
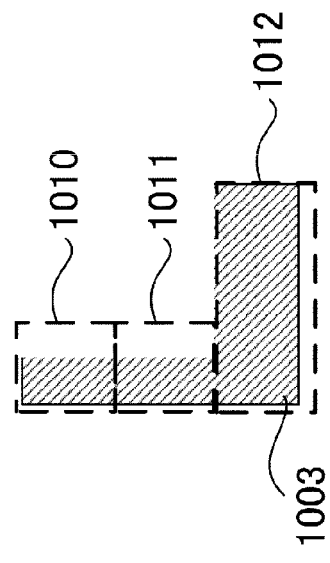
Figure 11A:
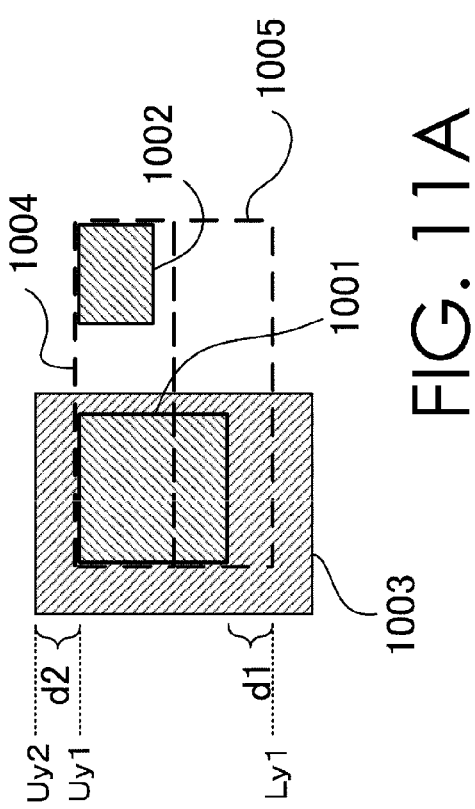
Figure 11C:
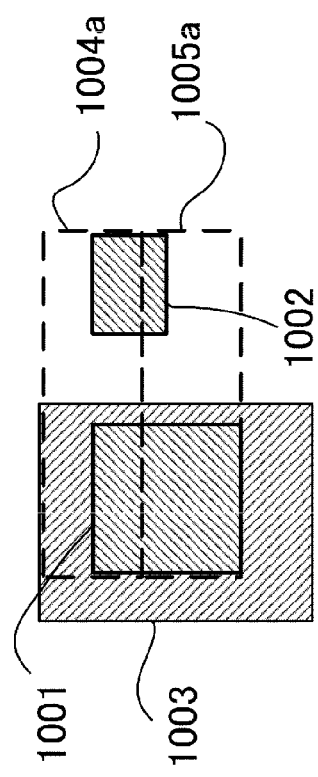

Meanwhile, upon measuring the regions 1001, 1002, it is possible to arrange the stripes in displacement as shown in FIG. 11C. In the foregoing case, the unmeasured region of the region 1003 will be displayed as an L-shape as shown in FIG. 11D. In other words, in order to measure the entire region 1003, it is necessary to newly measure regions 1010 to 1012. Based on the same calculation as the case of FIG. 11B, the distance that needs to be newly measured will be 10+10+25=45 mm and, therefore, in comparison to the case of making no adjustment, the scanning distance upon measuring the regions of low priority can be shortened by 15 mm. Note that, upon performing continuous scanning, while the length of the region to be measured and the scanning distance of the acoustic probe will slightly differ, these are considered to be the same in the present invention.

Step S3 in this embodiment disposes stripes in the inclusion region of a predetermined priority, and thereafter determines whether there is a region which overlaps with a region of one lower priority. Here, if there is an overlapping region, the arranged stripes are shifted in the sub scanning direction, and a position which will shorten the scanning distance upon measuring the regions of low priority is detected.

An example of shifting the stripes is now explained. In this explanation, the main scanning direction is the x axis and the sub scanning direction is the y axis.

In FIG. 11A, d1 is the distance of the excess portion of the measurement region of the region 1001 of priority 1 in the sub scanning direction. Since the region 1001 requires a height that is worth two stripes for the scanning, when the number of elements of the probe in the sub scanning direction is Eny and the element pitch is Ep, the required height of the scanning stripe can be calculated as 2×Eny×Ep.

Here, when the y coordinates of the uppermost part of the region of priority 1 is Uy1, and the y coordinates of the lowermost part of the region of priority 1 is Ly1, the excess range d1 of the region 1001 in the sub scanning direction will be (2×Eny×Ep−Uy1−Ly1). Note that, in the case of FIG. 11, Uy1 will be the y coordinates of the uppermost part of the region 1001, and Ly1 will be the y coordinates of the lowermost part of the region 1001.

In FIG. 11A, d2 is the difference between the uppermost part of the region of priority 2 and the uppermost part of the region of priority 1. Here, when the y coordinates of the uppermost part of the region of priority 2 is Uy2, d2 can be represented as Uy2−Uy1. Thus, if d1>0 and d2>0, there will be a margin for adjusting the stripe position at the upper part in the sub scanning direction.

Subsequently, whether d1 and d2 correspond to any one of the following three conditions is determined.

<Condition 1>

When d2 is a distance that is not smaller than the integral multiple (N times) of Eny×Ep; that is, when d2≥N×Eny×Ep is satisfied, N-number of stripes are disposed at the upper part of the measurement region of the region 1003 of priority 2. Here, when (d2−N×Eny×Ep)≤d1, the stripes for measuring the regions of priority 1 are shifted upward by (d2−N×Eny×Ep).

<Condition 2>

When d1≥d2, the stripes for measuring the regions of priority 1 are shifted to a position shifted upward by d2; that is, shifted to the upper end of the region 1003 of priority 2.

<Condition 3>

When d2<Eny×Ep, the upper limit position of the stripes for measuring the regions of priority 1 is shifted to the same position as the upper limit position of the regions of priority 1. The upper end of the stripes for measuring the regions of priority 2 is started from the same position as the upper limit of the regions of priority 2, and the measurement region thereof will overlap with the regions of priority 1.

Based on the foregoing method, candidates of the displacement position of the stripes for measuring the regions of priority 1 are determined. When the candidates of the displacement position are determined, the scanning distance upon measuring the regions of low priority is calculated, and, upon determining whether the scanning distance becomes shorter before and after shifting the stripes, the ultimate stripe position is determined.

Note that, when the scanning distance for measuring the regions of low priority will be the same regardless of how the stripes are shifted, the stripe position will remain unchanged.

As a result of performing the foregoing processing in addition to the processing of step S3 in the second embodiment, it is possible to reduce the scanning distance to the regions of low priority, and reduce the time required for performing measurement.

Note that, while this embodiment described an example of processing the actual scanning region of the highest priority, this embodiment may be applied to any priority so as long as there is one lower priority. Moreover, in this embodiment, when the overlapping with regions of one lower priority is determined and the stripe position is adjusted, but there are still three or more priorities, it is also possible to further determine the overlapping with regions of even lower priority.

Moreover, the method of shifting the stripe is not limited to the example illustrated in this embodiment. For example, there are cases where the measurement accuracy is improved and the scanning time is shortened based on scheduling in which the stripes are overlapped in the sub scanning direction according to the data accumulation, shape of probe, sensitivity distribution, and the like. Moreover, while this embodiment adopted a mode of moving the arrangement position after assigning the stripes, it is also possible to calculate the optimal position before assigning the stripes so as to directly assign the stripes.

Moreover, it is also possible to define the amount of displacement of the stripes in advance, and perform calculations of all patterns. For example, when the stripe adjustment margin is 5 mm, it is possible to perform 5 calculations by shifting the stripes 1 mm at a time, and adopting the stripe in which the scanning distance becomes shortest. Moreover, while this embodiment adjusted the position of the stripes so as to shorten the scanning distance upon measuring the regions of low priority, the scanning time may also be used as the determination criteria in substitute for the scanning distance.

The foregoing embodiments are merely an example, and the present invention may be implemented by being changed as needed to the extent that such change does not deviate from the gist of this invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-242271, filed on Nov. 4, 2011, which is hereby incorporated by reference herein its entirety.

What is claimed is:

1. An acoustic wave measuring apparatus, comprising:
an acoustic probe;
an input device for setting two or more regions of interest for an object, the regions of interest being set apart from each other;
a pointing device for setting priorities on the regions of interest that have been set;
a processor configured to
(i) determine, for each of the set priorities, an inclusion region including the regions of interest set with the priority,
(ii) divide each of the inclusion regions into a plurality of scanning regions and determine which of continuous measuring, fixed measuring, and non-measurement moving are performed for each of the scanning regions so as to shorten a total time required for scanning,
wherein the continuous measuring is a method of measuring while moving said acoustic probe at a first speed,
wherein the fixed measuring is a method in which a measurement is performed while stopping said acoustic probe and after the measurement said acoustic probe is moved at a speed faster than the first speed, and
wherein the non-measurement moving is a method of moving said acoustic probe without measuring at a speed faster than the first speed, and
(iii) determine a priority scanning order of a plurality of scanning regions having the same priority so as to shorten a movement distance of said acoustic probe; and
a movable mirror for scanning each of the inclusion regions according to the priority,
wherein said mirror scans the scanning regions according to the determined scanning order in each of the inclusion regions.

2. The acoustic wave measuring apparatus according to claim 1,
wherein, when a region of interest having a first priority and a region of interest having a second priority which is lower than the first priority overlap with each other, said mirror further performs scanning by excluding the overlapping region upon scanning the region of interest having the second priority, and uses, as information to be acquired from the overlapping region, information that has been acquired upon scanning the region of interest having the first priority.

3. The acoustic wave measuring apparatus according to claim 2, wherein, when assigning a scanning region to the inclusion region having the first priority, said processor is further configured to determine an assignment position of the scanning region so as to shorten a scanning distance upon measuring the region of interest having the second priority.

4. The acoustic wave measuring apparatus according to claim 1,
wherein said acoustic probe further includes an ultrasound source configured to transmit ultrasound waves to the object, and to receive reflected waves from the object, and
wherein the first speed is calculated based on a drive frequency of said acoustic probe and an element pitch of said acoustic probe in a main scanning direction.

5. The acoustic wave measuring apparatus according to claim 1, further comprising a light source for irradiating light onto the object,
wherein said acoustic probe is further configured to receive a photoacoustic signal generated from the object based on a photoacoustic effect caused by the light, and
wherein the first speed is calculated based on a light-emitting frequency of said light source and an element pitch of said acoustic probe in a main scanning direction.

6. The acoustic wave measuring apparatus according to claim 5, wherein a cumulative number of the photoacoustic signal is determined according to a designation by a user, and wherein the first speed is calculated by using the cumulative number.

7. The acoustic wave measuring apparatus according to claim 1, further comprising a camera configured to capture an image of an object, wherein a display associated with said input device presents an image of the object captured by the camera to a user, and the input device receives a setting of the region of interest from the user.

8. The acoustic wave measuring apparatus according to claim 7, wherein said processor is further configured to determine the inclusion region by converting a coordinate system of the image of the object captured by said camera into a coordinate system in the apparatus, and to determine the scanning order based on the coordinate system in the apparatus.

9. The acoustic wave measuring apparatus according to claim 1, wherein said processor is further configured to set conditions of photoacoustic measurements for each region of interest which has the same priority.

10. A method of controlling an acoustic wave measuring apparatus having an acoustic probe, comprising the steps of:

receiving a designation of two or more regions of interest for an object;

receiving a designation of priorities on the designated regions of interest of which has been received in said regions of interest designation receiving step;

determining, for each of the designated priorities, an inclusion region including the regions of interest;

dividing each of the inclusion regions into a plurality of scanning regions;

determining which of continuous measuring, fixed measuring, and non-measurement moving are performed for each of the scanning regions so as to shorten a total time required for scanning, wherein the continuous measuring is a method of measuring while moving the acoustic probe at a first speed, wherein the fixed measuring is a method in which a measurement is performed while stopping the acoustic probe and after the measurement the acoustic probe is moved at a speed faster than the first speed, and wherein the non-measurement moving is a method of moving the acoustic probe without measuring at a speed faster than the first speed;

determining a scanning order of a plurality of scanning regions having the same priority so as to shorten a movement distance of the acoustic probe; and scanning each of the inclusion regions according to the priority, wherein, in each inclusion region, the scanning regions are scanned according to the determined scanning order.

* * * * *